(12) United States Patent
Zwiers et al.

(10) Patent No.: US 7,464,602 B2
(45) Date of Patent: Dec. 16, 2008

(54) PRESSURE TRANSMISSION CATHETER WITH SHEATH

(75) Inventors: Lynn M. Zwiers, Lino Lake, MN (US); Gregg Lichtscheidl, Roseville, MN (US); Eric Rudie, Maple Grove, MN (US)

(73) Assignee: Transoma Medical, Inc., St. Paul, MN (US)

(*) Notice: Subject to any disclaimer, the term of this patent is extended or adjusted under 35 U.S.C. 154(b) by 0 days.

(21) Appl. No.: 11/479,932

(22) Filed: Jun. 30, 2006

(65) Prior Publication Data

US 2008/0000303 A1 Jan. 3, 2008

(51) Int. Cl.
*G01L 7/10* (2006.01)
(52) U.S. Cl. .................................................. 73/729.2
(58) Field of Classification Search .............. 73/729.2, 73/706, 751

See application file for complete search history.

(56) References Cited

U.S. PATENT DOCUMENTS

| 4,160,448 A | 7/1979 | Jackson |
| 5,048,532 A | 9/1991 | Hickey |
| 2005/0070844 A1* | 3/2005 | Chow et al. ............. 604/95.04 |
| 2005/0278020 A1* | 12/2005 | Wang et al. ............... 623/1.44 |
| 2006/0184165 A1* | 8/2006 | Webster et al. ................ 606/41 |

FOREIGN PATENT DOCUMENTS

| WO | WO94/12097 | 6/1994 |
| WO | WO96/04846 | 2/1996 |

* cited by examiner

*Primary Examiner*—Andre J Allen
(74) *Attorney, Agent, or Firm*—Fish & Richardson P.C.

(57) ABSTRACT

Methods and apparatus for sensing pressure are disclosed. One disclosed pressure measuring device comprises a pressure transmission catheter including a stem portion and a sheath fixed to the stem portion. The disclosed sheath comprises a wall defining a cavity that is in fluid communication with a stem lumen defined by the stem portion. The disclosed sheath has a first transverse extent and a second transverse extent that is different from the first transverse extent.

24 Claims, 10 Drawing Sheets

PRESSURE TRANSMISSION CATHETER WITH SHEATH

FIELD OF THE INVENTION

The present invention relates to pressure sensing devices.

BACKGROUND OF THE INVENTION

Pressure measurement devices can be used to sense numerous internal body pressures in humans and animals. Examples of pressures that may be sensed include pulmonary pressure, venous pressure, left ventricle pressure, intracranial pressure, and bladder pressure. These measurements provide an important tool for medical research and clinical diagnosis. For example, hydrocephalus and head injuries can cause body fluids to build up within the brain. The resulting fluid pressure buildup can result in death or serious brain damage. In another example, urinary dysfunction can cause fluid pressure to build up in the bladder. In a further example, intrapleural pressure measurements can be used to monitor the respiration of infants who have been identified as being at risk for sudden infant death syndrome.

Blood pressure measurements are particularly important for medical research and diagnosis for a variety of reasons. Such measurements provide researchers with insight into the physiology and functioning of the heart. Blood pressure measurements also provide researchers with useful information regarding the safety and efficacy of pharmaceuticals and the toxicity of chemicals. By transducing blood pressure into a signal waveform, a variety of useful parameters can be extracted. These parameters provide valuable information for the diagnosis of heart disease.

BRIEF SUMMARY OF THE INVENTION

The present disclosure relates generally to methods and apparatus for sensing pressure. One disclosed pressure measuring device comprises a pressure transmission catheter including a stem portion and a sheath fixed to the stem portion. The disclosed sheath comprises a wall defining a cavity that is in fluid communication with a stem lumen defined by the stem portion. The disclosed sheath has a first transverse extent and a second transverse extent that is different from the first transverse extent.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
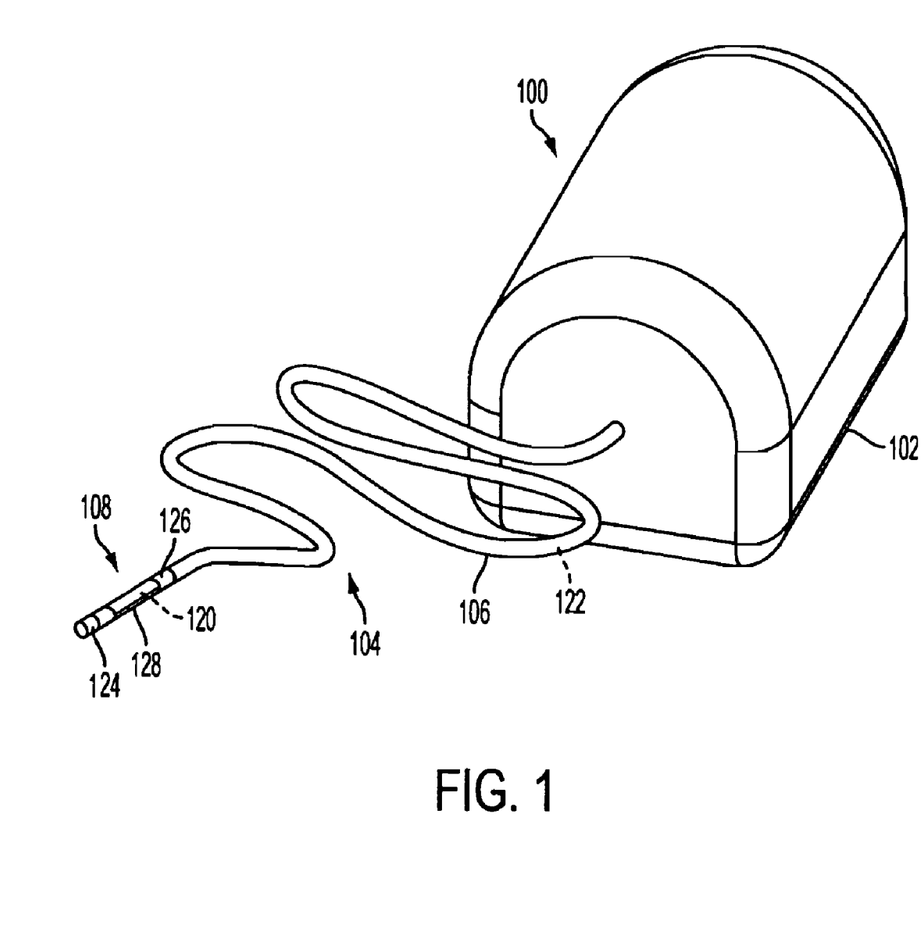
FIG. 1 is a perspective view showing a pressure measurement device 100 in accordance with an exemplary embodiment of the present invention.

FIG. 1 is a perspective view showing a pressure measurement device 100 in accordance with an exemplary embodiment of the present invention. Pressure measurement device 100 comprises an electronics housing 102 and a pressure transmission catheter 104. Pressure transmission catheter 104 comprises a stem portion 106 and a sheath 108. Sheath 108 defines a cavity 120 that is in fluid communication with a stem lumen 122 defined by stem portion 106.

In the embodiment of FIG. 1, sheath 108 comprises a first waist portion 124, a second waist portion 126, and an intermediate portion 128 located between first waist portion 124 and second waist portion 126. With reference to FIG. 1, it will be appreciated that first waist portion 124 and second waist portion 126 of sheath 108 are both have a generally cylindrical shape. In FIG. 1, intermediate portion 128 of sheath 108 is shown generally having the geometry of a partially flattened tube.

Figure 2:
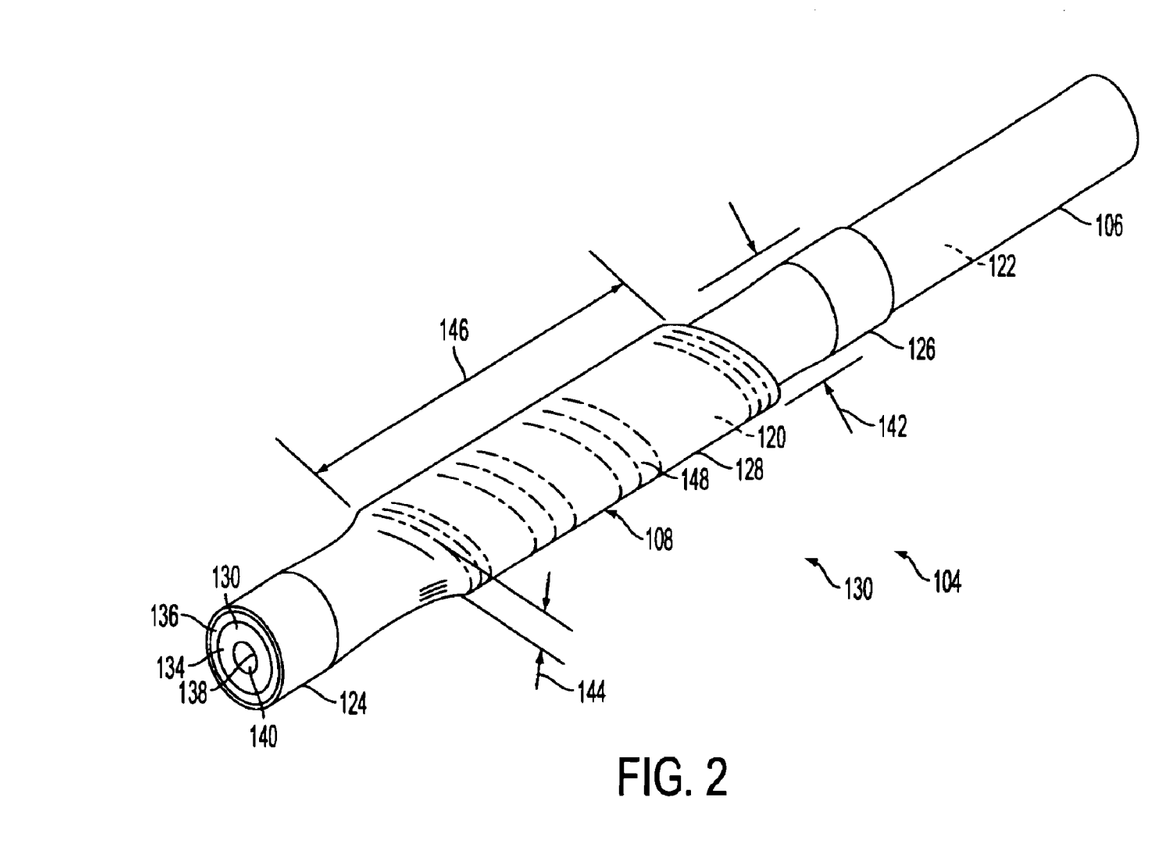
FIG. 2 is a perspective view of a distal portion 130 of the pressure transmission catheter shown in the previous figure.

FIG. 2 is a perspective view of a distal portion 130 of pressure transmission catheter 104 shown in the previous figure. In the embodiment of FIG. 2, second waist portion 126 of sheath 108 is fixed to stem portion 106. First waist portion 124 of sheath 108 is coupled to a strut 134 by a seal 136. A distal portion 130 of strut 134 is visible in FIG. 2. With reference to FIG. 2, it will be appreciated that strut 134 defines a strut lumen 138. In the embodiment of FIG. 2, the end of strut lumen 138 is sealed with a plug 140. In some embodiments of the present invention, strut 134 extends between the first waist portion and the second waist portion of the sheath. When this is the case, the strut may provide increased axial rigidity to the sheath.

With reference to FIG. 2, it will be appreciated that first waist portion 124 and second waist portion 126 of sheath 108 are both have a generally cylindrical shape. In the embodiment of FIG. 2, an intermediate portion 128 is disposed between first waist portion 124 and second waist portion 126. In the embodiment of FIG. 2, intermediate portion 128 of sheath 108 has the geometry of a partially flattened tube so that intermediate portion 128 has a first transverse extent 142 and a second transverse extent 144 that is different from the first transverse extent 142. In the embodiment of FIG. 2, intermediate portion 128 of sheath 108 has an axial extent 146. With reference to FIG. 2, it will be appreciated that axial extent 146 is greater than both first transverse extent 142 and second transverse extent 144.

Sheath 108 defines a cavity 120 that is in fluid communication with a stem lumen 122 defined by stem portion 106. Also in the embodiment of FIG. 2, intermediate portion 128 of sheath 108 has an outer surface 148 having a surface area. In the embodiment of FIG. 2, the surface area of outer surface 148 is greater than the lateral cross-sectional area of stem lumen 122. This arrangement may to reduce the likelihood that overgrowth will adversely affect the measuring capability of the pressure measurement device.

Figure 3:
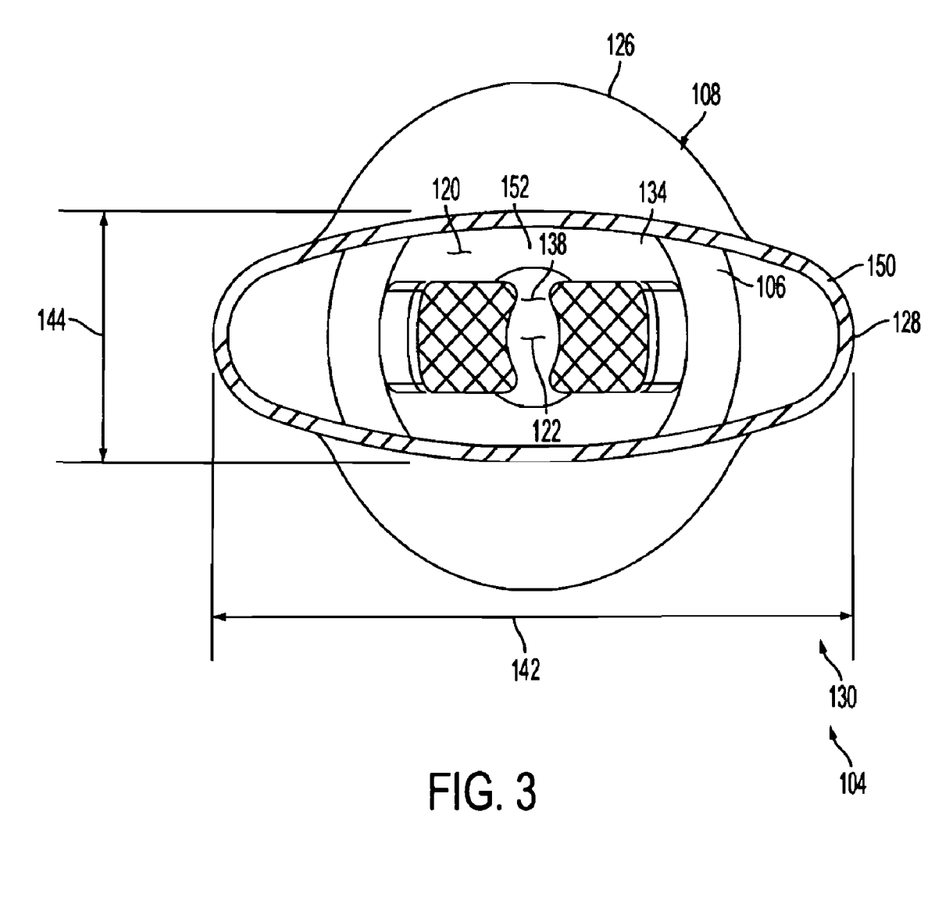
FIG. 3 is a cross-sectional view of the distal portion of the pressure transmission catheter shown in the previous figure.

FIG. 3 is a cross-sectional view of distal portion 130 of pressure transmission catheter 104 shown in the previous figure. In the embodiment of FIG. 3, second waist portion 126 of sheath 108 can be seen disposed about stem portion 106. In FIG. 3, strut 134 can be seen disposed in a cavity 120 defined by wall 150 of sheath 108. With reference to FIG. 3, it will be appreciated that strut 134 comprises a tubular member 152 defining a strut lumen 138. In the embodiment of FIG. 3, strut lumen 138 fluidly communicates with a stem lumen 122 defined by stem portion 106.

With reference to FIG. 3, it will be appreciated that second waist portion 126 of sheath 108 has a generally circular shape. With continuing reference to FIG. 3, it will be appreciated that intermediate portion 128 of sheath 108 has the geometry of a partially flattened tube so that intermediate portion 128 has a first transverse extent 142 and a second transverse extent 144 that is different from the first transverse extent 142. In the embodiment of FIG. 3, wall has a generally uniform wall thickness.

Figure 4:
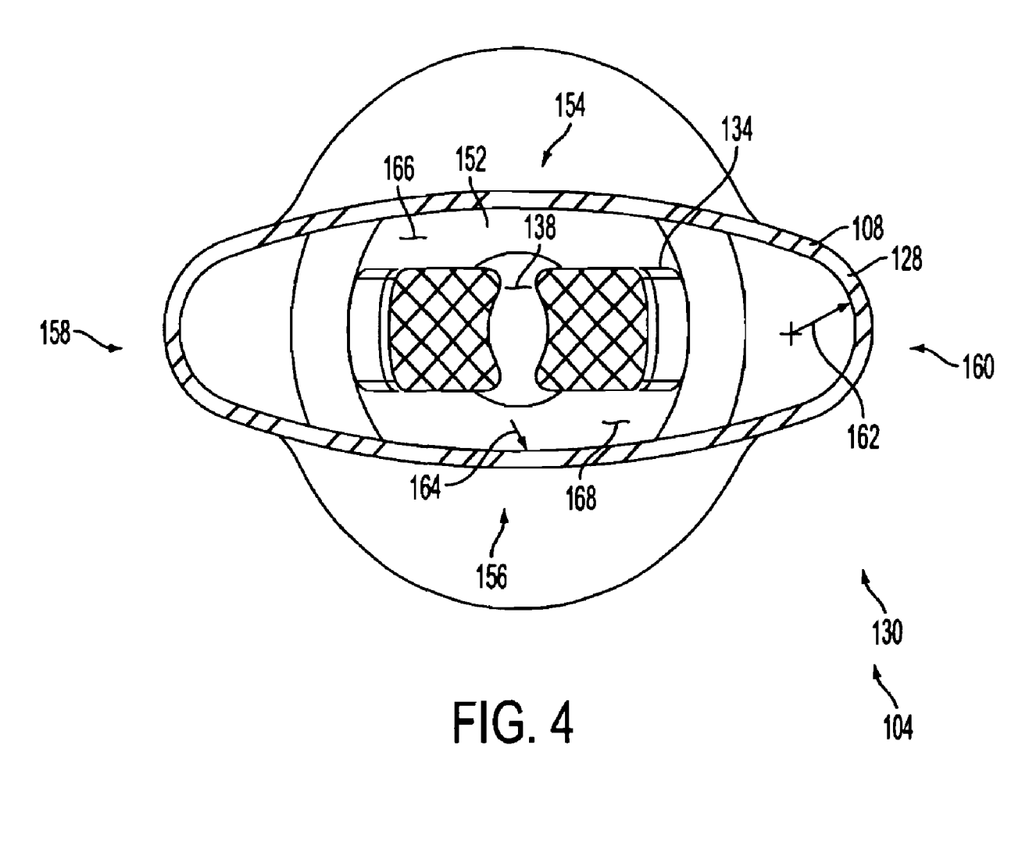
FIG. 4 is an additional cross-sectional view of the distal portion of the pressure transmission catheter shown in the previous figure.

FIG. 4 is an additional cross-sectional view of distal portion 130 of pressure transmission catheter 104 shown in the previous figure. In the embodiment of FIG. 4, intermediate portion 128 of sheath 108 comprises a first major side 154, a second major side 156, a first minor side 158, and a second minor side 160. In FIG. 4, each side is shown having a generally convex shape. In the embodiment of FIG. 4, each minor side has greater convexity than each major side. Also in the embodiment of FIG. 4, each minor side has a first radius 162 and each major side has a second radius 164 that is greater than first radius 162. In some applications, the geometry illustrated in FIG. 4 provides a pressure sensing sheath in which each major side is more sensitive to pressure changes than each minor side.

With reference to FIG. 4, it will be appreciated that strut 134 comprises a tubular member 152 defining a strut lumen 138. Tubular member 152 also defines a first cutout 166 and a second cutout 168. In the embodiment of FIG. 4, first major side 154 of sheath 108 extends into first cutout 166 defined by strut 134. Also in the embodiment of FIG. 4, second major side 156 of sheath 108 extends into second cutout 168 defined by strut 134.

Sheath 108 may comprise various metallic and non-metallic materials without deviating from the spirit and scope of the present invention. Examples of metallic materials that may be suitable in some applications include stainless steel, Elgiloy, MP-35N, titanium, gold, and platinum.

In some useful embodiments of the present invention, sheath 108 comprises a resilient and/or reversibly deformable material. For example, sheath 108 may comprise an elastomeric material. The term elastomeric generally refers to a rubber-like material (e.g., a material which can experience about a 5% deformation and return to the undeformed configuration). Examples of elastomeric materials include rubber (e.g., natural rubber, silicone rubber, nitrile rubber, polysulfide rubber, etc.), thermoplastic elastomer (TPE), butyl, polyurethane, and neoprene.

Sheath 108 may comprise, for example, a thin walled silicone rubber tube. Silicone rubber that may be suitable in some applications is commercially available from Dow Corning Corporation of Midland, Mich. which identifies this silicone rubber using the SILASTIC trademark. Alternatively, sheath 108 may comprise a thin walled silicone urethane copolymer tube. Silicone urethane copolymers that may be suitable in some applications are commercially available from The Polymer Technology Group of Berkeley, Calif. Sheath 108 may also comprise a thin walled polycarbonate urethane. Polycarbonate urethanes that may be suitable in some applications are commercially available from The Polymer Technology Group of Berkeley, Calif.

Stem portion 106 may comprise various metallic and non-metallic materials without deviating from the spirit and scope of the present invention. Examples of metallic materials that may be suitable in some applications include stainless steel, Elgiloy, MP-35N, titanium, gold, and platinum. Examples of non-metallic materials that may be suitable in some applications include polycarbonate, polyurethane (PU), polyethylene (PE), polypropylene (PP), and polyvinylchloride (PVC), fluoropolytetrafluoroethylene (PTFE), and ePTFE.

Figure 5:
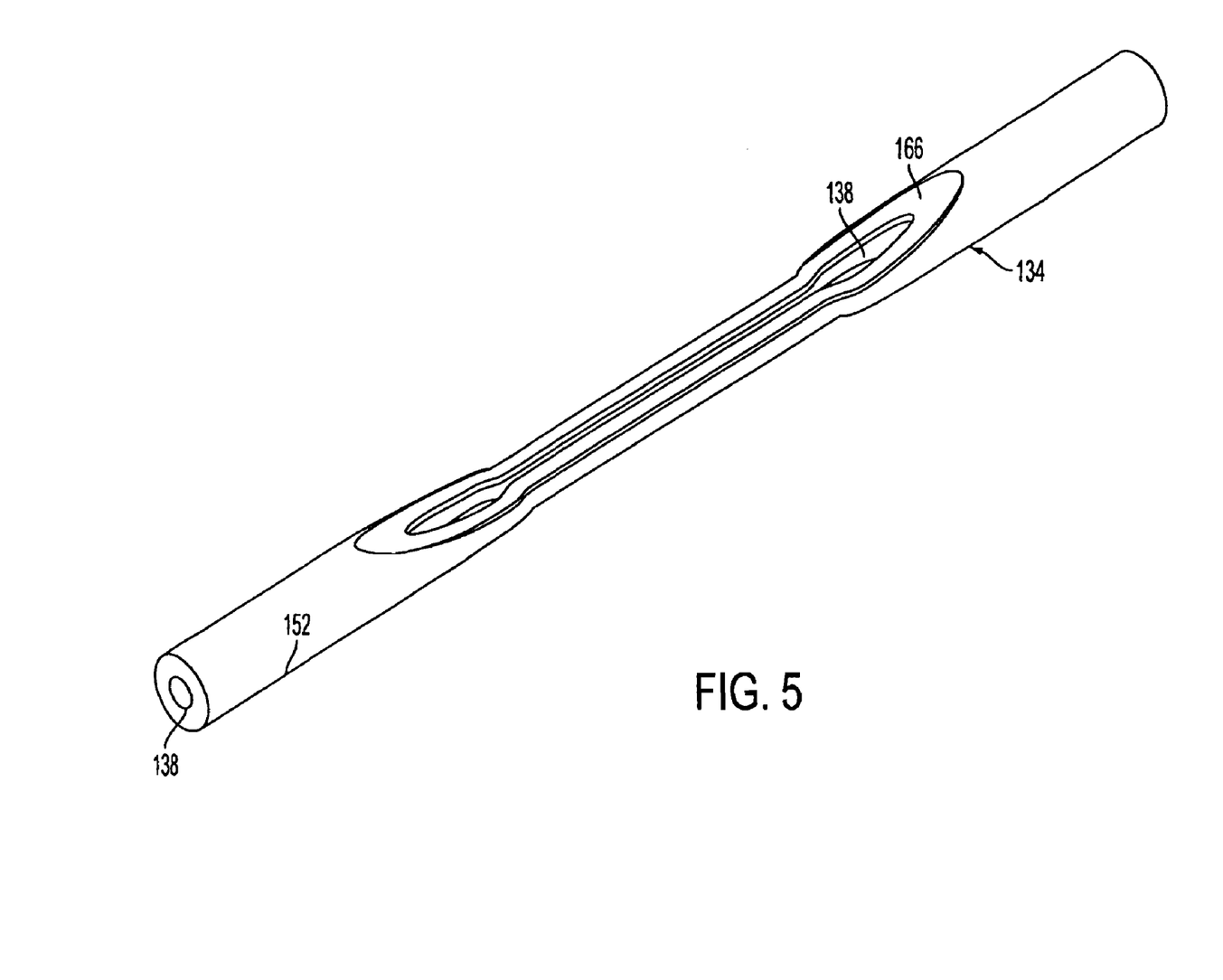
FIG. 5 is an isometric view of the strut shown in the previous figure.

FIG. 5 is an isometric view of strut 134 shown in the previous figure. Strut 134 comprises a tubular member 152 defining a strut lumen 138. In the embodiment of FIG. 5, tubular member 152 defines a first cutout 166 that fluidly communicates with strut lumen 138.

Figure 6:
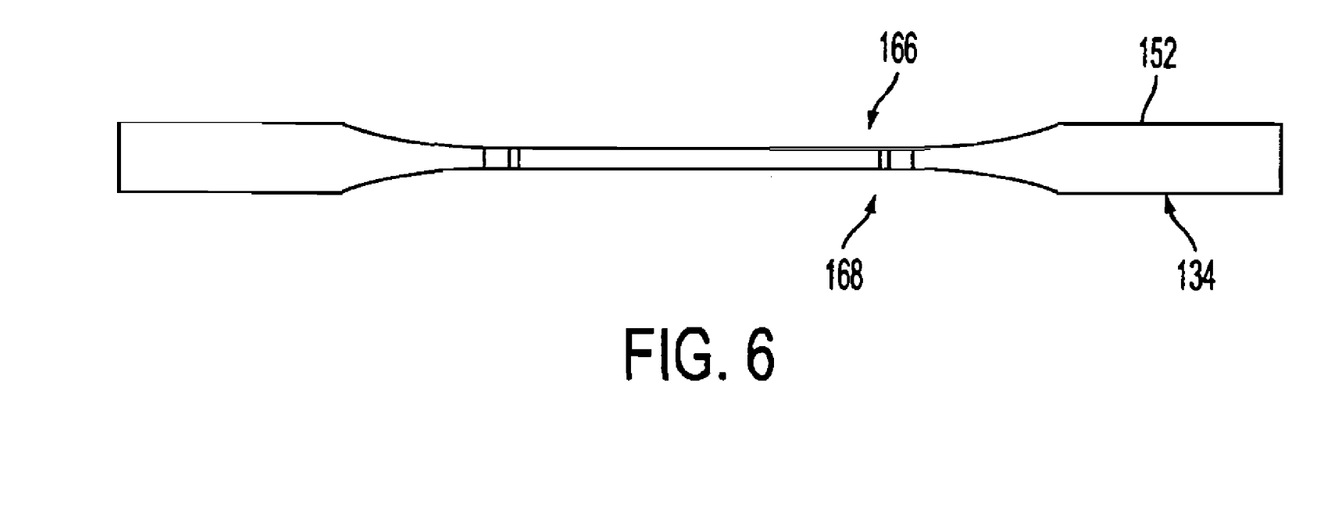
FIG. 6 is a side view of the strut shown in the previous figure.

FIG. 6 is a side view of strut 134 shown in the previous figure. With reference to FIG. 6, it will be appreciated that tubular member 152 of strut 134 defines a first cutout 166 and a second cutout 168.

Figure 7:
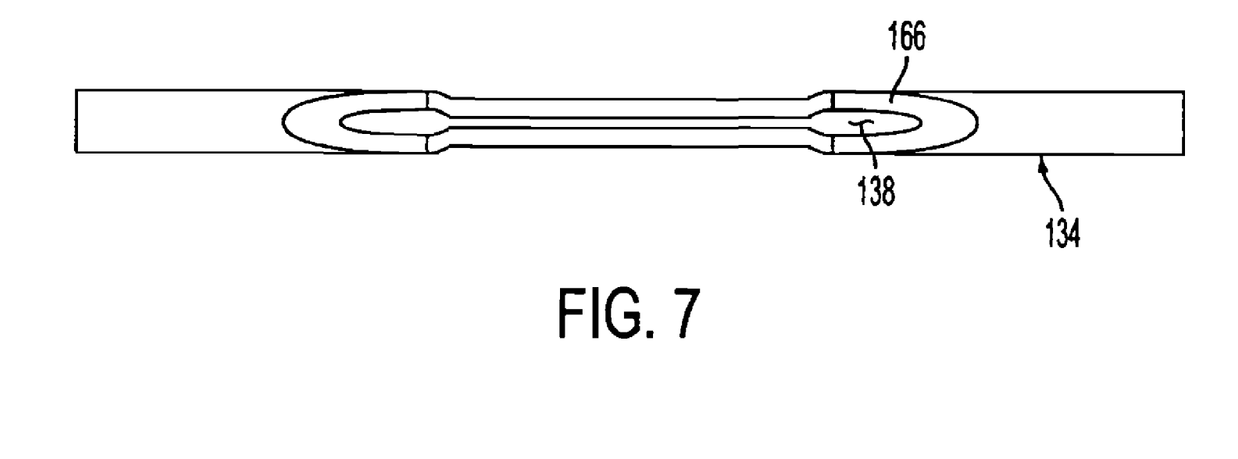
FIG. 7 is a top view of the strut shown in the previous figure.

FIG. 7 is a top view of strut 134 shown in the previous figure. With reference to FIG. 7, it will be appreciated a first cutout 166 defined by tubular member 152 fluidly communicates with strut lumen 138.

Figure 8:
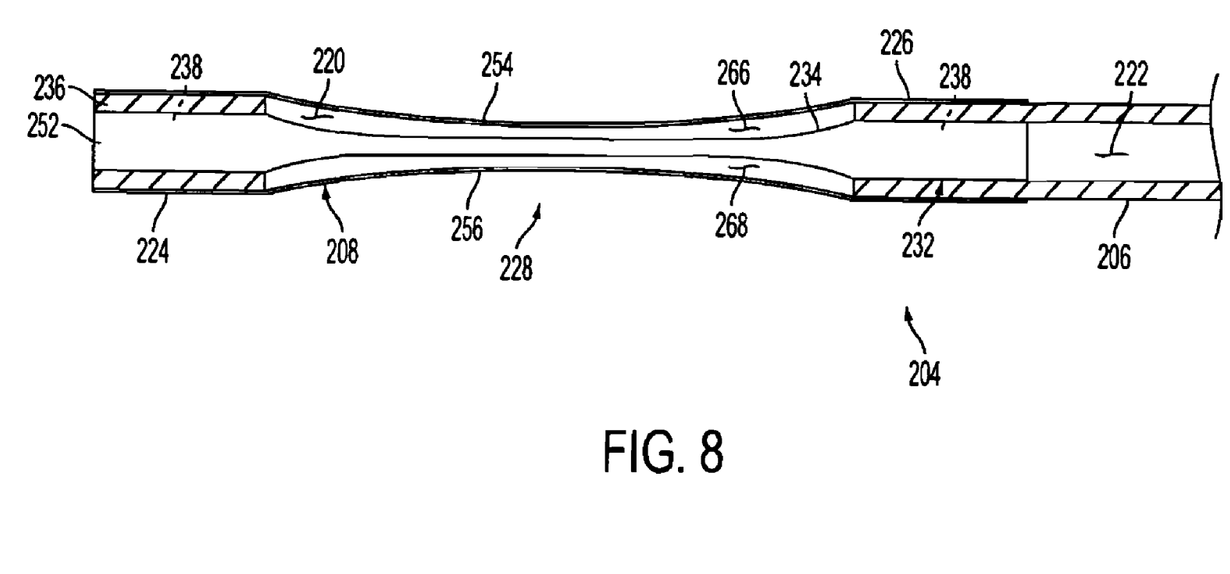
FIG. 8 is a partial cross sectional view of a pressure transmission catheter including a strut that is similar to the strut shown in the previous figure.

FIG. 8 is a partial cross sectional view of a pressure transmission catheter 204 including a strut 234 that is similar to the strut shown in the previous figure. Pressure transmission catheter 204 comprises a stem portion 206 and a sheath 208. In the embodiment of FIG. 8, a proximal portion 232 of a strut 234 is fixed to stem portion 206 of pressure transmission catheter 204. Sheath 208 defines a cavity 220 that is in fluid communication with a stem lumen 222 defined by stem portion 206.

In the embodiment of FIG. 8, sheath 208 comprises a first waist portion 224, a second waist portion 226, and an intermediate portion 228 located between first waist portion 224 and second waist portion 226. In the embodiment of FIG. 8, second waist portion 226 of sheath 208 is fixed to stem portion 206. First waist portion 224 of sheath 208 is coupled to strut 234 by a seal 236.

Strut 234 comprises a tubular member 252 defining a strut lumen 238. In the embodiment of FIG. 8, tubular member 252 defines a first cutout 266 that fluidly communicates with strut lumen 238. Also in the embodiment of FIG. 8, tubular member 252 defines a second cutout 268 that fluidly communicates with strut lumen 238. In the embodiment of FIG. 8, a first major side 254 of sheath 208 extends into first cutout 266 defined by strut 234. Also in the embodiment of FIG. 8, a second major side 256 of sheath 208 extends into second cutout 268 defined by strut 234.

Figure 9:
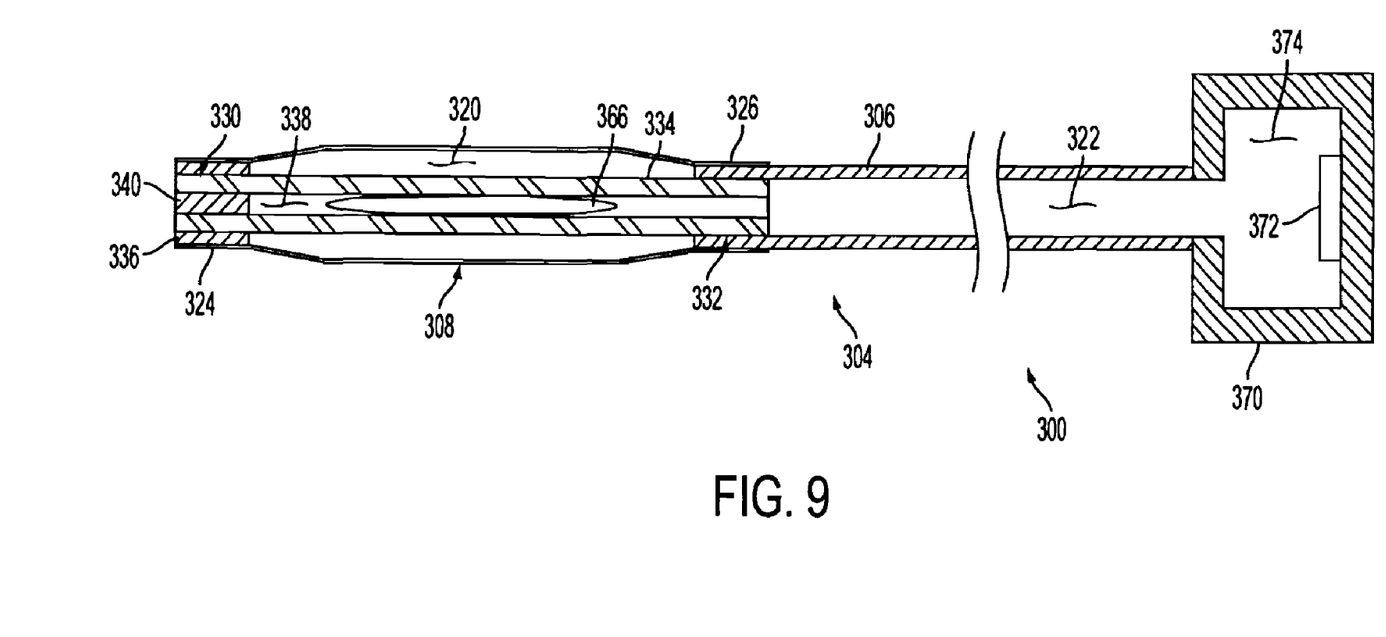
FIG. 9 is a somewhat diagrammatic cross-sectional view of a pressure measurement device in accordance with an exemplary embodiment of the present invention.

FIG. 9 is a somewhat diagrammatic cross-sectional view of a pressure measurement device 300 in accordance with an exemplary embodiment of the present invention. Pressure measurement device 300 comprises a sensor housing 370 and a pressure transmission catheter 304. Pressure transmission catheter 304 comprises a stem portion 306 and a sheath 308. Stem portion 306 defines a stem lumen 322 that fluidly communicates with an interior 374 defined by sensor housing 370. A pressure sensor 372 is disposed in interior 374 of sensor housing 370. Pressure sensor 372 may comprise, for example, a piezo-resistive Wheatstone bridge silicon strain gauge. Pressure sensors that may be suitable in some applications are commercially available from Sensonor of Horten, Norway.

In the embodiment of FIG. 9, a proximal portion 332 of a strut 334 is fixed to stem portion 306 of pressure transmission catheter 304. A distal portion 330 of strut 334 is coupled to a first waist portion 324 of a sheath 308 by a seal 336. With reference to FIG. 9, it will be appreciated that strut 334 defines a strut lumen 338 that fluidly communicates with stem lumen 322 defined by stem portion 306. A cutout 366 defined by strut 334 is also visible in FIG. 9. Cutout 366 of is disposed in fluid communication with strut lumen 338 and a cavity 320 defined by sheath 308. In the embodiment of FIG. 9, the end of strut lumen 338 is sealed with a plug 340.

In the embodiment of FIG. 9, second waist portion 326 of sheath 308 is fixed to stem portion 306. With reference to FIG. 9, it will be appreciated that strut 334 extends between first waist portion 324 of sheath 308 and a second waist portion 326 of sheath 308. Accordingly, strut 334 may provide increased axial rigidity to sheath 308.

Figure 10:
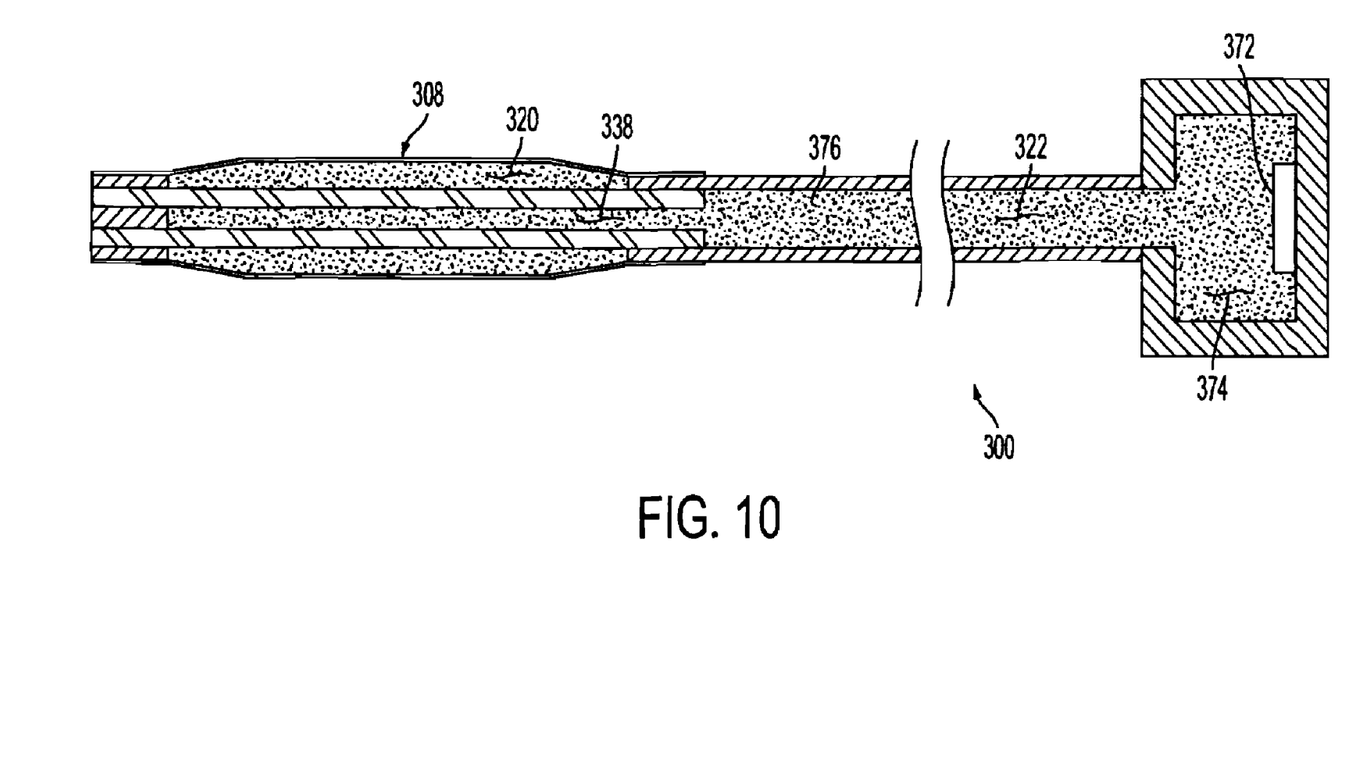
FIG. 10 is an additional diagrammatic cross-sectional view of the pressure measurement device shown in the previous figure.

FIG. 10 is an additional diagrammatic cross-sectional view of pressure measurement device 300 shown in the previous figure. In the embodiment of FIG. 10, a pressure transmitting fluid 376 is disposed in pressure measurement device 300 for transferring pressure between sheath 308 and pressure sensor 372. With reference to FIG. 10 it will be appreciated that pressure transmitting fluid 376 is disposed in cavity 320, strut lumen 338, stem lumen 322, and sensor housing interior 374.

Those skilled in the art will recognize that the present invention may be manifested in a variety of forms other than the specific embodiments described herein. Accordingly, departures in form and detail may be made without departing from the spirit and scope of the present invention as described in the appended claims. The entire disclosure of all patents and patent applications mentioned in this document are hereby incorporated by reference herein.

What is claimed is:

1. An implantable pressure sensor, comprising:
   a pressure transducer with a mechanical sensing input and an electrical output that provides an indication of a sensed pressure level; and
   an elongate pressure transmission catheter comprising an outer covering that forms an inner cavity, and a pressure transmission substance contained within the inner cavity;
   wherein at least a portion of the outer covering is formed to have a cross-sectional shape that is a partially flattened circle; and
   wherein the pressure transmission catheter is formed so that external pressure forces acting upon an outside surface of the portion of the outer covering having partially-flattened-circle-cross-sectional-shape compress the pressure transmission substance within the inner cavity and are conveyed via the pressure transmission substance to the mechanical sensing input of the pressure transducer to provide an indication of a pressure level of an environment within which the pressure transmission catheter is positioned.

2. The implantable pressure sensor of claim 1, wherein the cross-sectional shape is defined by at least two different local radii of curvature.

3. The implantable pressure sensor of claim 1, wherein the at least a portion of the outer covering has a first transverse extent, a second transverse extent different from the first transverse extent, and an axial extent, and wherein the axial extent is greater than both the first transverse extent and the second transverse extent.

4. The implantable pressure sensor of claim 1, wherein the at least a portion of the outer covering has a first major side, a second major side opposite the first major side, a first minor side, and a second minor side opposite the first minor side.

5. The implantable pressure sensor of claim 4, wherein the major sides are more compliant than the minor sides.

6. The implantable pressure sensor of claim 4, wherein the major sides offer less resistance to deflection than the minor sides.

7. The implantable pressure sensor of claim 4, wherein the minor sides are more rigid than the major sides.

8. The pressure measurement device of claim 4, wherein each of the minor sides has a first radius of curvature and each of the major sides has a second radius or curvature that is greater than the first radius of curvature.

9. The implantable pressure sensor of claim 4, wherein the major sides and the minor sides each have a generally convex shape, and each of the minor sides have greater convexity than each of the major sides.

10. The implantable pressure sensor of claim 4, wherein the major sides are more sensitive to pressure than are the minor sides.

11. The implantable pressure sensor of claim 1, wherein the at least a portion of the outer covering is substantially free of convolutions.

12. The implantable pressure sensor of claim 1, wherein the at least a portion of the outer covering has uniform thickness.

13. The implantable pressure sensor of claim 1, wherein the at least a portion of the outer covering comprises an elastomeric material.

14. The implantable pressure sensor of claim 1, further comprising first and second waist portions, each having generally cylindrical shape, wherein the at least a portion of the outer covering is disposed between the first waist portion and the second waist portion.

15. The implantable pressure sensor of claim 14, further comprising a strut extending between the first waist portion and the second waist portion.

16. The implantable pressure sensor of claim 15, wherein the strut provides axial stability.

17. The implantable pressure sensor of claim 15, wherein the strut defines a first cutout space that extends along a first side of the strut.

18. The implantable pressure sensor of claim 17, wherein the outer covering extends into the cutout space.

19. The implantable pressure sensor of claim 17, wherein the strut further defines a second cutout space that extends along a second side of the strut opposite the first side of the strut.

20. The implantable pressure sensor of claim 1, wherein the at least a portion of the outer covering formed to have a cross-sectional shape that is a partially flattened circle comprises a first material, and a remainder of the elongate pressure transmission catheter comprises a second material different from the first material.

21. The implantable pressure sensor of claim 20, wherein the first material comprises an elastomeric material and the second material comprises a non-elastomeric material.

22. The implantable pressure sensor of claim 20, wherein the first material is more flexible than the second material.

23. The implantable pressure sensor of claim 20, wherein the first material has a first modulus of elasticity and the second material has a second modulus of elasticity that is greater than the first modulus of elasticity.

24. An implantable pressure sensor, comprising:
   a pressure transducer with a mechanical sensing input and an electrical output that provides an indication of a sensed pressure level; and
   an elongate pressure transmission catheter comprising an outer covering that forms an inner cavity, and a pressure transmission substance contained within the inner cavity;

wherein at least a portion of the outer covering is formed to have a non-circular cross-sectional shape; and wherein the pressure transmission catheter is formed so that external pressure forces acting upon an outside surface of the portion of the outer covering having non-circular- cross-sectional-shape compress the pressure transmission substance within the inner cavity and are conveyed via the pressure transmission substance to the mechanical sensing input of the pressure transducer to provide an indication of a pressure level of an environment within which the pressure transmission catheter is positioned.

* * * * *